(12) United States Patent
Yang et al.

(10) Patent No.: US 12,409,110 B2
(45) Date of Patent: Sep. 9, 2025

(54) COMPOSITION WITH SUPERABSORBENT POLYMER

(71) Applicant: SHISEIDO COMPANY, LTD., Tokyo (JP)

(72) Inventors: Binhua Yang, East Windsor, NJ (US); Nancy Hanna, East Windsor, NJ (US); Daisuke Suzuki, East Windsor, NJ (US)

(73) Assignee: SHISEIDO COMPANY, LTD., Tokyo (JP)

( * ) Notice: Subject to any disclaimer, the term of this patent is extended or adjusted under 35 U.S.C. 154(b) by 563 days.

(21) Appl. No.: 17/774,845

(22) PCT Filed: Dec. 22, 2020

(86) PCT No.: PCT/IB2020/062356
§ 371 (c)(1),
(2) Date: May 5, 2022

(87) PCT Pub. No.: WO2021/130677
PCT Pub. Date: Jul. 1, 2021

(65) Prior Publication Data
US 2022/0387266 A1 Dec. 8, 2022

Related U.S. Application Data

(60) Provisional application No. 62/954,159, filed on Dec. 27, 2019.

(51) Int. Cl.
*A61K 8/04* (2006.01)
*A61K 8/31* (2006.01)
*A61K 8/73* (2006.01)
*A61K 8/81* (2006.01)
*A61Q 19/00* (2006.01)

(52) U.S. Cl.
CPC ............. *A61K 8/042* (2013.01); *A61K 8/31* (2013.01); *A61K 8/73* (2013.01); *A61K 8/8147* (2013.01); *A61Q 19/00* (2013.01); *A61K 2800/34* (2013.01); *A61K 2800/48* (2013.01)

(58) Field of Classification Search
CPC ........ A61K 8/042; A61K 8/31; A61K 8/8147; A61K 2800/34; A61K 2800/48; A61Q 19/00
See application file for complete search history.

(56) References Cited

U.S. PATENT DOCUMENTS 9,549,891 B2    1/2017   Tanner et al.
2014/0093461 A1 4/2014   Mac Dermott et al.
2015/0023895 A1 1/2015   Finley et al.
2015/0342864 A1 12/2015  Labatut
2016/0081895 A1* 3/2016  Elliott .................... A61K 8/345
                                                    424/60
2018/0221256 A1 8/2018   Sunkel

FOREIGN PATENT DOCUMENTS

CN   105451819 A        3/2016
FR     2975287 A1 *    11/2012   ............... A61K 8/42
FR   2 989 884 A1      11/2013
FR   2 999 919 A1       6/2014
JP   2018-518516 A      7/2018
WO   WO-2013/087926 A1  6/2013
WO   WO-2017/004108 A1  1/2017

OTHER PUBLICATIONS

Machine translation of Fageon, et al., FR-2975287-A1 [online]. Espacenet [retrieved on Oct. 18, 2024]. Retrieved from teh internet: <https://worldwide.espacenet.com/patent/>. (Year: 2012).*
Office Action issued in corresponding European Patent Application No. 20830340.4 dated Dec. 8, 2023 (4 pages).
International Searching Authority, "International Search Report," issued in connection with International Patent Application No. PCT/IB2020/062356, dated Mar. 29, 2021.
International Searching Authority, "Written Opinion," issued in connection with International Patent Application No. PCT/IB2020/062356, dated Mar. 29, 2021.
Nikkol product profiles, Author: Nikko chemicals Co, Publication data: Nikko Chemicals Co, 2010, Retrieved from the internet: URL: http://www.kenjohn.com.tw/uploads/download/20170824111418887.pdf, p. 51.
Garnier, Canada, Eye Gel, Mintel GNPD [online], Apr. 2016, ID#3945589, [retrieved on May 15, 2023 (May 15, 2023)], Internet URL: https://portal.mintel.com.
Lancome, France, The Illuminating & Anti-Fatigue Cooling Eye Gel, Mintel GNPD [online], Aug. 2017, ID#5008815, [retrieved on May 5, 2023 (May 5, 2023)], Internet URL: https://portal.mintel.com.
Office Action issued in corresponding Japanese Patent Application No. 2022-530937, dated May 30, 2023.
Nikko Chemicals Co., Ltd., "Nikkol Product Profiles", pp. 1-69, Jan. 2010.
Office Action issued in corresponding Chinese Patent Application No. 202080081603.2 dated Mar. 21, 2024 (8 pages).
Office Action issued in corresponding Japanese Patent Application No. 2022-530937 dated Nov. 14, 2023 (7 pages).
International Preliminary Report on Patentability issued in PCT Application No. PCT/IB2020-062356, mailing date of Jul. 7, 2022.
Office Action issued in corresponding Chinese Patent Application No. 202080081603.2 dated Nov. 29, 2024.

* cited by examiner

*Primary Examiner* — Genevieve S Alley
(74) *Attorney, Agent, or Firm* — Foley & Lardner LLP

(57) ABSTRACT

Provided is a cosmetic composition which includes at least one superabsorbent polymer; at least one water soluble emollient; and at least one thickener.

10 Claims, 4 Drawing Sheets

COMPOSITION WITH SUPERABSORBENT POLYMER

PRIORITY

The present application claims priority under 37 U.S.C. § 371 to International Patent Application No. PCT/IB2020/062356, filed Dec. 22, 2020, which claims priority to and the benefit of U.S. Provisional Application No. 62/954,159 filed Dec. 27, 2019. The contents of these applications are hereby incorporated by reference in their entireties.

FIELD

The present disclosure relates in general to cosmetic compositions and more specifically to cosmetic compositions, which include a superabsorbent polymer, and their methods of making and using.

SUMMARY

One embodiment is a cosmetic composition comprising: at least one superabsorbent polymer; at least one water soluble emollient; and at least one thickener.

FIGURES

DETAILED DESCRIPTION

Figure 1:
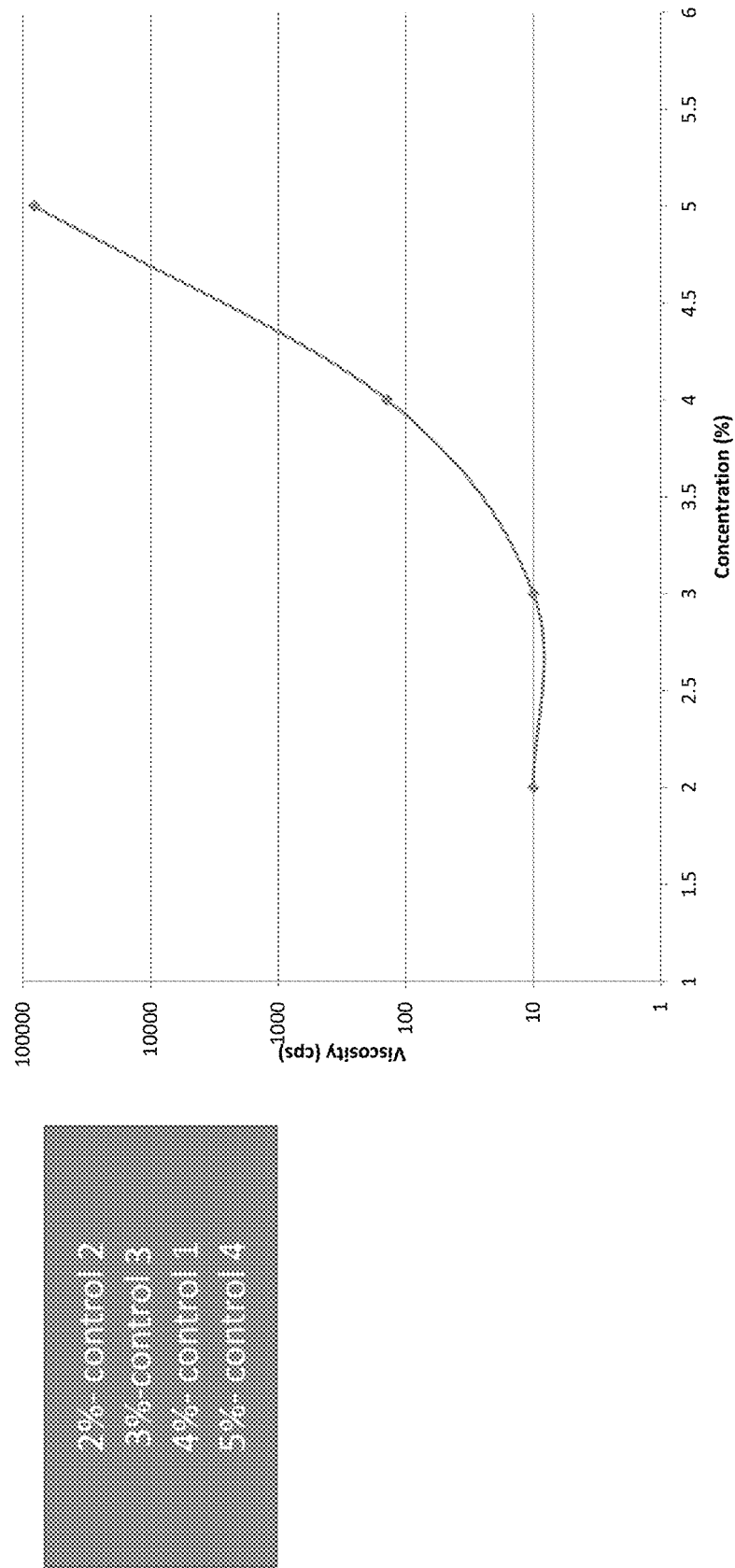
FIG. 1 is a plot of viscosity of a cosmetic composition versus a concentrations of sodium acrylates crosspolymer-2. This plot illustrates a thickening behavior of sodium acrylates crosspolymer-2.
Figure 2:
FIG. 2 is a photograph of cosmetic compositions with different concentrations of sodium acrylates crosspolymer-2.
Figure 3:
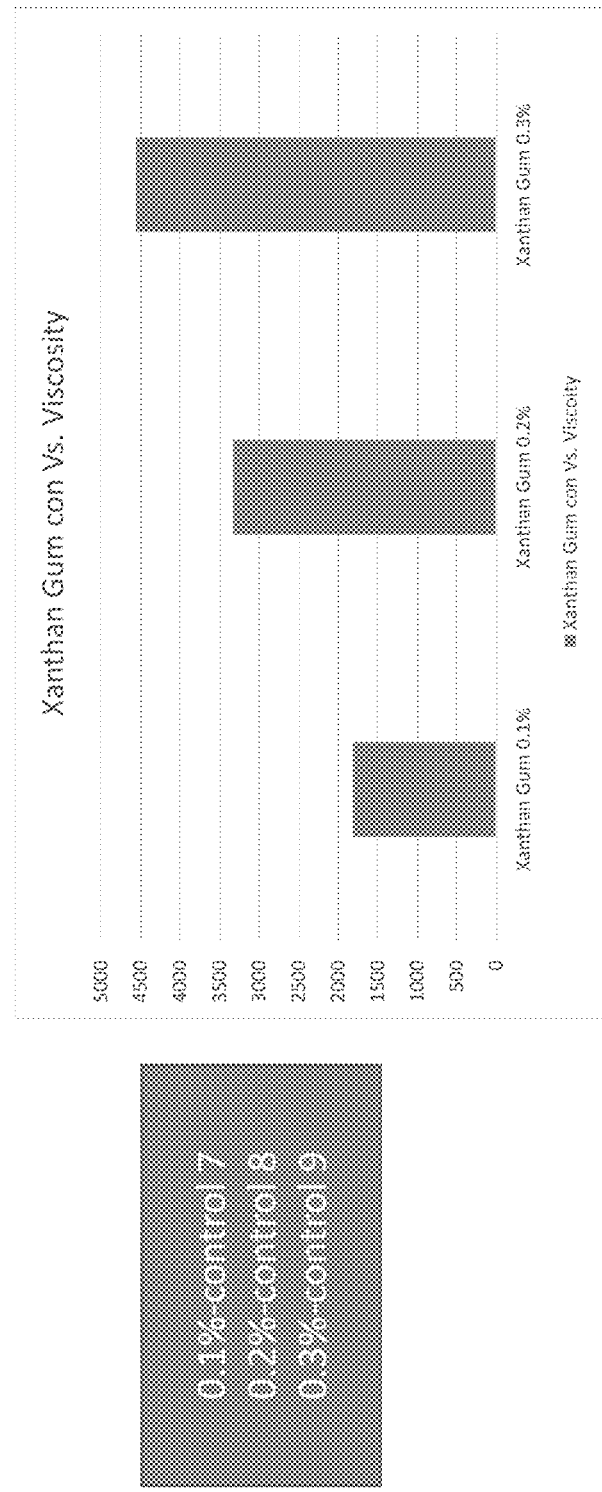
FIG. 3 is a chart demonstrating an effect of xanthan gum concentration on viscosity of a cosmetic composition.
Figure 4:
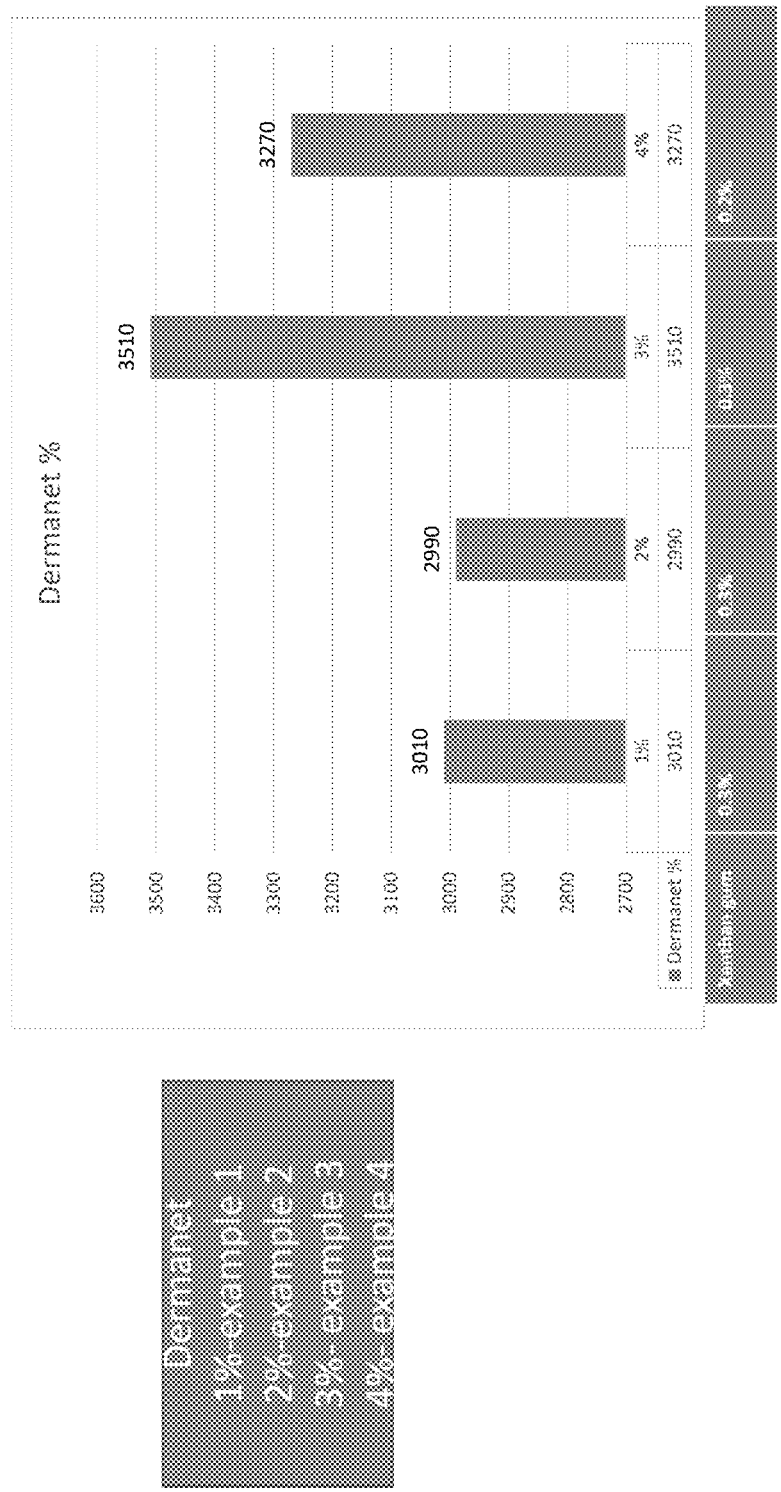
FIG. 4 is a chart demonstrating an effect of a concentration of a microfluidized squalane and xanthan gum composition on viscosity of a cosmetic composition.

Unless otherwise specified "a" or "an" means one or more.

As used herein, the term "about" placed before a specific numeric value may mean ±20% of the numeric value; ±18% of the numeric value, ±15% of the numeric value; ±12% of the numeric value; ±8% of the numeric value; ±5% of the numeric value; ±3% of the numeric value; ±2% of the numeric value; ±1% of the numeric value or ±0.5% of the numeric value.

Unless otherwise specified, all content information for ingredients of compositions expressed as % refers to % by mass, relative to the total mass of the composition, unless specified otherwise.

Cosmetic compositions, which contain a superabsorbent polymer, water and a surfactant are disclosed, for example, in the French Patent No. FR 2,989,884; U.S. patent application publications Nos. US20150342864; US 2014093461; US20160081895; US2018221256; US2015023895; and U.S. Pat. No. 9,549,891;

The inventors developed a cosmetic composition, which contains at least one superabsorbent polymer, at least one water soluble emollient and at least one thickener, which may be stable. As used herein, the term "stable" means that the composition does not undergo any of separation of its ingredients, a change in color and/or a change in texture (e.g., cushion and elastomer-like feel) over time, such as up to two years at ambient conditions (e.g., 25° C./65% RH) and four weeks at accelerated conditions (e.g., 50° C./65% RH).

Preferably, the cosmetic composition is silicone-free. However, it may have sensory properties, such as silkiness, softness, weightlessness and/or cushiony feel, similar to the ones of a cosmetic composition containing silicone. In other words, a texture of the cosmetic composition may be similar to the one of a silicone containing cosmetic composition.

As used herein, the term "silicone-free" means that a total content in the cosmetic composition of any silicone based ingredient(s), such as silicon oils, silicone elastomers, and/or silicone resins, is less than 1 mass %, or less than 0.5 mass % or less than 0.3 mass or less than 0.2 mass % or less than 0.1 mass %. Preferably, the silicone-free composition does not contain any silicone based ingredient(s).

Applications of the composition are not limited to cosmetic applications, such as makeup. For example, in some embodiments, applications of the cosmetic composition may include but are not limited to applications in a skin care product, in a sun care product, in a color cosmetics product, in a deodorant or in a hair product.

In some embodiments, the cosmetic composition may be used alone. In other words, the composition may be applied alone, without another composition, to a keratinous surface or substrate, such as skin or hair, of a subject, such as a human. Yet, in some embodiments, the cosmetic composition may be used together with another composition, which may be, for example, a cosmetic or skincare composition, such as a makeup composition. For example, in certain embodiments, the cosmetic composition may be applied to the keratinous surface or substrate before another composition is applied.

Preferably, the cosmetic composition can be used as a primer, meaning that it may be deposited on the keratinous substrate as an initial product for delivering hydrating, plumping, blurring and/or long wear effect to the keratinous surface or substrate.

In some embodiments, the cosmetic composition may have one or multiple of unique sensory properties, such as those described above. In some embodiments, the cosmetic composition may provide a weightlessness, e.g., no heavy or sticky feel. In some embodiments, the cosmetic composition may be long lasting. For example, the cosmetic composition may stay on a keratinous surface or substrate for at least 4 hours or at least 6 hours or at least 8 hours or at least 10 hours or at least 12 hours or at least 14 hours or at least 16 hours or at least 18 hours or at least 20 hours without interruption of esthetical appearance. In some embodiments, the cosmetic composition may provide fresh/cooling water effect.

In some embodiments, the cosmetic composition, alone or with another composition, such as a cosmetic or skincare composition, may be used to provide a blurring effect and make pores, wrinkles and/or any other imperfections of a keratinous surface or substrate, such as skin, look less visible.

Preferably, the cosmetic composition is a non-emulsion composition, which may mean that it is not composed of water and oil phases. Additionally, the non-emulsion composition may not require the use of surfactants to stay stable.

Preferably, the cosmetic composition is a gel. For example, in some embodiments, the cosmetic composition may be a soft and cushion-like gel having silky and slippery texture.

In some embodiments, the cosmetic composition may have a viscosity ranging from about 2000 cps to about 8000 cps, from about 2500 cps to about 5000 cps or from about 3000 cps to about 3600 cps.

In some embodiments, the cosmetic composition may have from clear and transparent to hazy and/or milky visual appearance.

In some embodiments, the cosmetic composition may contain water, from about 70% to about 90% as per total mass (weight) of the composition, such as at least 70 mass % or at least 72 mass % or at least 74 mass % or at least 76 mass % or at least 78 mass % or at least 79 mass % of water.

In some embodiments, the at least one superabsorbent polymer may include, for example, but is not limited to, at least one of superabsorbent polymers disclosed in U.S. Patent Application Publication No. 2018/0221256, which is incorporated herein by reference in its entirety. As used herein, the term "superabsorbent polymer" may refer to a polymer, which can absorb and retain an amount of liquid, such as water, which has a mass significantly higher than a mass of the polymer itself. For example, the superabsorbent polymer can absorb and retain an amount of liquid, such as water, which has a mass at least 3 times, or at least 5 times or at least 8 times or at least 12 times or at least 15 times or at least 18 times or at least 20 times than a mass of the polymer itself.

In some embodiments, the at least one superabsorbent polymer may include at least one of cross-linked sodium acrylates, acrylate grafted starches or mixtures thereof.

In some embodiments, the at least one superabsorbent polymer may include, but is not limited to, at least one superabsorbent polymer selected from the group consisting of sodium polyacrylate, sodium acrylate, sodium polyacrylate starch, sodium acrylates crosspolymer-2 or mixtures thereof. For example, in certain embodiments, the at least one superabsorbent polymer may comprise sodium acrylates crosspolymer-2. Sodium acrylates crosspolymer-2 is commercially available, for example, as Barcril AV or Aqua Keep 10SH-NFC from Kobo.

An amount of the at least one superabsorbent polymer in the composition may vary. For example, it may be from about 2 mass % to about 4.5 mass %, from about 2.5 mass % to about 4.0 mass % or from about 3 mass % to about 3.5 mass %.

In some embodiments, the composition may contain at least one thickener. The at least one thickener may be selected from, but is not limited, to natural thickeners, synthetic thickeners and their combinations. For example, in some embodiments, the at least one thickener may include at least one natural thickener. Yet in some embodiments, the at least one thickener may include at least one synthetic thickener. Suitable thickeners are disclosed, for example, in U.S. Patent Application Publication No. US 2017007512 and U.S. Pat. No. 6,689,345, each of which is incorporated herein in its entirety. Examples of suitable thickeners may include, but are not limited, to succinoglycan, xanthan gum, carrageenan, gellan gum, starch, hydroxyalkylcellulose, pullulan, carbomer, sodium silicate, magnesium silicate, bentonite, acrylamide copolymer, sodium acryloyl dimethyl taurine/hydroxyethyl acrylate copolymer, agar, polyurethane, and hydrophobic polyether polyurethane.

An amount of the at least one thickener in the cosmetic composition may vary. For example, the at least one thickener may be present at range from about 0.1 mass % to about 0.3 mass %, from about 0.15 mass % to about 0.28 mass %, or from about 0.2 mass % to about 0.25 mass %.

In some embodiments, the at least one water soluble emollient may comprise a microfluidized emollient composition, i.e. a water soluble composition of a microfluidized emollient. Microfluidized emollient compositions are disclosed, for example, in U.S. Patent Application Publication No. US 20160081895, which is incorporated herein by reference in its entirety.

The term "microfluidized" may refer to a fluid, particles of which may be geometrically constrained to a small, typically on a sub-millimeter scale, at which capillary penetration may govern mass transport. In some embodiments, the particle size of the microfluidized substance may be from about 0.1 micron to 2 micron or from about 0.2 micron to about 1.5 micron or from about 0.5 micron to about 1 micron.

The term "emollient" may refer to a substance having ability of softening and smoothing a keratinous surface or substrate, such as skin and hair.

In some embodiments, the at least one water soluble emollient may include microfluidized squalane.

In some embodiments, the microfluidized emollient composition may include an emollient, a solvent, and a stabilizing agent.

In some embodiments, the emollient of the microfluidized emollient composition may be selected from but not limited to hydrocarbons, including hydrocarbons of natural origin, including saturated branched hydrocarbons. Non-limiting examples of the emollient of the microfluidized emollient composition may be squalane, which may be produced, for example, from an animal source, such as shark liver oil, a vegetable oil, such as an olive oil or a jojoba oil, or a mixture thereof; or an oil, such as a plant based oil, such as a jojoba oil.

In some embodiments, the solvent of the microfluidized emollient composition may be selected from water, humectants and mixtures thereof.

In some embodiments, the stabilizing agent of the microfluidized emollient composition may be selected from surfactants, including but not being limited to triglycerides, fatty acids and carbohydrates and mixtures thereof. A non-limiting example of a stabilizing agent utilized may be hydrogenated lecithin.

In some embodiments, the water soluble microfluidized emollient composition may comprise glycerin, which may be vegetable glycerin; water; squalane, which may be microfluidized squalane; hydrogenated lecithin; or a mixture thereof.

In some embodiments, the water soluble microfluidized emollient composition may comprise glycerin, which may be vegetable glycerin; water, jojoba oil, which may be microfluidized jojoba oil; hydrogenated lecithin; or a mixture thereof.

Such water soluble microfluidized emollient composition may be present in the cosmetic composition in an amount from about 1 mass % to about 5 mass % or from about 2 mass % to about 4 mass % or from about 2.5 mass % to about 3 mass %.

An example of water soluble microfluidized emollient composition utilized in the composition is the emollient composition containing water, (vegetable) glycerin, squalane and hydrogenated lecithin. Such a composition is commercially available as Dermanet Squalane from Blue Sun International, Miami, Florida, U.S.A.

Another example of water soluble microfluidized emollient composition utilized in the composition is the emollient composition containing water, (vegetable) glycerin, jojoba oil and hydrogenated lecithin. Such a composition is commercially available as Dermanet Jojoba from Blue Sun International, Miami, Florida, U.S.A.

In some embodiments, the water soluble microfluidized emollient composition may contain squalane or jojoba oil.

In some embodiments, the micronized emollient present in the water soluble microfluidized emollient composition may be present at the range from about from 1 mass % to about 25 mass % or from about 2 mass % to about 20 mass %, such as from about 3 mass % to about 15 mass % per mass of the water soluble microfluidized emollient composition.

pigments, esters, softening/conditioning agents, preservatives, solvents, surfactants and combinations thereof.

In some embodiments, the additional optional ingredients may be present in an amount from about 1 mass % to about 25 mass %, from 2 mass % to about 20 mass %, from 5 mass % to 20 mass % or from 10 mass % to 20 mass %.

Embodiments described herein are further illustrated by, though in no way limited to, the following working examples.

Example

TABLE 1

Studied cosmetic compositions

| Raw Material | Control 1 | Control 2 | Control 3 | Control 4 | Control 5 | Control 6 | Control 7 | Control 8 | Control 9 | Example 1 | Example 2 | Example 3 | Example 4 |
|---|---|---|---|---|---|---|---|---|---|---|---|---|---|
| Deionized water | 84.05 | 86.05 | 85.05 | 83.05 | 80.85 | 83.55 | 84.05 | 83.95 | 83.85 | 82.85 | 81.85 | 80.85 | 79.95 |
| 1,3 butylene glycol | 8.00 | 800 | 8.00 | 8.00 | 8.00 | 8.00 | 8.00 | 8.00 | 8.00 | 8.00 | 8.00 | 8.00 | 8.00 |
| BARCRIL AV (sodium acrylates crosspolymer-2) | 4.00 | 2.00 | 3.00 | 5.00 | 4.00 | 4.00 | 4.00 | 4.00 | 4.00 | 4.00 | 4.00 | 4.00 | 4.00 |
| Glycerin (glycerine 99.7% Acidchem) | 3.00 | 3.00 | 3.00 | 3.00 | 3.00 | 3.00 | 3.00 | 3.00 | 3.00 | 3.00 | 3.00 | 3.00 | 3.00 |
| Phenoxyethanol | 0.90 | 0.90 | 0.90 | 0.90 | 0.90 | 0.90 | 0.80 | 0.80 | 0.80 | 0.80 | 0.80 | 0.80 | 0.80 |
| Disodium EDTA (EDTA 2 Na•2H$_2$O) | 0.05 | 0.05 | 0.05 | 0.05 | 0.05 | 0.05 | 0.05 | 0.05 | 0.05 | 0.05 | 0.05 | 0.05 | 0.05 |
| Xantlian gum (Keltrol ®) | | | | | 0.20 | 0.20 | 0.10 | 0.20 | 0.30 | 0.30 | 0.30 | 0.30 | 0.20 |
| Glycerin, water, squalene, hydrogenated lecithin (Dermanet Squalane) | | | | | 3.00 | | | | | 1.00 | 2.00 | 3.00 | 4.00 |
| Squalane | | | | | | 0.30 | | | | | | | |
| Test | | | | | | | | | | | | | |
| Viscosity | 140 | 10 | 10 | 81830 | 8200 | 9700 | 1820 | 3330 | 4560 | 3010 | 2990 | 3510 | 3270 |
| Stability | Failed | Failed | Failed | OK | OK | Failed | OK | OK | OK | OK | OK | OK | OK |
| Texture | smooth gel/ Fresh water break | N/A | N/A | Thick gel, takes time to rub in | Quick absorption, Silky emollience feel | Long Play time, heavy feel. | Soft gel/ fresh water break | Soft gel/ fresh water break | Slightly sticky | Soft and smooth gel/ less cushion | Soft and smooth gel/ cushion | Soft and smooth gel/ cushion | Soft and smooth gel/ more cushion |
| Visual Appearance | gel with slight liquid on top | Liquid, two layers gel | Liquid, two layers gel | Very thick gel | Transparent gel/ blueish | Hazy/ white gel | Transparent gel | Transparent gel | Transparent gel | Transparent gel | Transparent gel | Transparent gel | Transparent gel |

In some embodiments, the cosmetic composition may include from about 2 mass % to about 4.5 mass % of a superabsorbent polymer, from about 1 mass % to about 5 mass % of a microfluidized emollient composition, from about 0.1 mass % to about 0.3 mass % of a thickener and at least about 70 mass % of water.

For example, the cosmetic composition may include from about 2 mass % to about 4.5 mass % of a superabsorbent polymer, such as sodium acrylates crosspolymer-2, from about 0.2 mass % to about 0.3 mass % of a thickener, such as xanthan gum, from about 1 mass % to about 5 mass % of a microfluidized emollient composition, such as a microfluidized squalane composition, and at least about 70 mass % of water.

In addition, the cosmetic composition may include one or more additional optional ingredients, such as waxes, color Table 1 presents ingredients of studied cosmetic compositions and reports results of viscosity, stability, texture and visual appearance evaluation of these compositions.

Based on Table 1, the composition of control 6 containing squalane (non-microfluidized form) failed stability tests, as well as its texture, play time and viscosity are out of the acceptance ranges. Additionally, control examples 1-3 demonstrate that the absence of the thickener contributes to stability failure, as well as to viscosity being too low. In contrary, example 4 shows that the increased amount of the superabsorbent increases viscosity above the desired level, even that the thickener is not present at all. Based on the evaluation of controls 7-9, it is believed that the presence of both, the superabsorbent polymer and the thickener may contribute to increasing stability and help to obtain the desired viscosity, however the absence of the water soluble composition of microfluidized emollient causes that the cushiony texture is out of the acceptance. Control 5 exemplifies that the use of all three ingredients, i.e. a superabsorbent polymer; a water soluble emollient; and a thickener, but at a level, which may be out of the preferred ranges (as described above), allows obtaining a stable composition characterized by alleviated viscosity and not entirely desired texture. Examples 1-4 demonstrate that utilizing of the superabsorbent polymer, water soluble composition of microfluidized emollient and thickener at specific levels, allows obtaining compositions, having silicone-like properties.

TABLE 2

| Ingredient | Mass % |
|---|---|
| Phase A | |
| Deionized water | 79.35 |
| Disodium EDTA (EDTA 2 Na•2H₂O) | 0.05 |
| Phase B | |
| Glycerin (glycerine 99.7% Acidchem) | 3 |
| Xanthan gum (Keltrol ®) | 0.2 |
| Phase C | |
| 1,3 butylene glycol | 5 |
| Sodium hyaluronate | 0.1 |
| Sodium Acrylates Crosspolymer-2 (Barcril AV) | 4 |
| Phase D | |
| 1,3 butylene glycol | 3 |
| Phenoxyethanol | 0.8 |
| Phase E | |
| Water, phenoxyethanol, sodium carrageenan, maris sal | 1.5 |
| Phase F | |
| Glycerin, water, squalene, hydrogenated lecithin (Dermanet Squalane) | 3 |

Table 2 illustrates how ingredients of an exemplary cosmetic composition can be distributed between different phases used for preparing compositions.

The compositions were prepared as follows:

Phase A was prepared by adding deionized water and EDTA in a main beaker and then mixing them at a room temperature.

Phase B was prepared by premixing glycerine and xanthan gum. Then the mixture was added to the main beaker.

Phase C was prepared by premixing 1, 3 butylene glycol and Barcril AV, making sure that they are mixed well. Then mixture was added to the main beaker, where all the ingredients were mixed well for 10-15 minutes.

Phase D was prepared by adding a preservative, such as phenoxyethanol, to the main beaker and mixing the ingredients in the main beaker well.

Phases A-F were mixed in a glass beaker with HEIDON overhead stirrer and a prop mixer.

Viscosity measurements were performed in 2 oz glass jars using Brookfield Viscometer with spindles #3 and #4 at ambient conditions (25 C/65% RH).

Stability and texture evaluation were conducted visually for the samples kept for four weeks at 50 C. The following characteristics were observed:

Passed: clear/transparent and smooth gel, silky feel, soft gel, smooth gel, cushiony feel, no separation and/or color within composition Failed: water break from gel, too thin (viscosity below 1500 cps), too thick (viscosity above 8500 cps), separation and color/transparency change to hazy milky observed.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A cosmetic composition comprising:
   at least about 70% of water;
   1 mass % to 4.5 mass % of sodium acrylates crosspolymer-2;
   1 mass % to 5 mass % of a microfluidized emollient water soluble composition comprising glycerin, water, squalane, and hydrogenated lecithin; and
   0.1 mass % to 0.3 mass % of xanthan gum,
   wherein the composition has a viscosity from about 2000 cps to about 5000 cps.

2. The cosmetic composition of claim 1, which is a silicone free composition.

3. The cosmetic composition of claim 1, which is a non-emulsion.

4. The cosmetic composition of claim 1, which is a gel.

5. The cosmetic composition of claim 1, comprising about 4 mass % of sodium acrylates crosspolymer-2, from about 0.2 mass % to about 0.3 mass % of xanthan gum, and from about 1 mass % to about 5 mass % of the microfluidized emollient composition.

6. A cosmetic method comprising applying the cosmetic composition of claim 1 to a keratinous surface.

7. The cosmetic composition of claim 1, wherein the microfluidized emollient water soluble composition consists of glycerin, water, squalane, and hydrogenated lecithin.

8. The cosmetic composition of claim 1, wherein cosmetic composition consists of:
   at least about 70% of water;
   1 mass % to 4.5 mass % of sodium acrylates crosspolymer-2;
   1 mass % to 5 mass % of a microfluidized emollient water soluble composition consisting of glycerin, water, squalane, and hydrogenated lecithin;
   0.1 mass % to 0.3 mass % of xanthan gum; and
   1 mass % to 25 mass % of one or more additional ingredients selected from the group consisting of waxes, color pigments, esters, softening/conditioning agents, preservatives, solvents, surfactants and combinations thereof.

9. The cosmetic composition of claim 8, wherein the one or more additional ingredients are selected from the group consisting of waxes, color pigments, preservatives, solvents, surfactants and combinations thereof.

10. The cosmetic composition of claim 8, wherein the one or more additional ingredients are selected from the group consisting of preservatives, solvents, surfactants and combinations thereof.

* * * * *